United States Patent [19]

Kurtz et al.

[11] Patent Number: 4,648,874

[45] Date of Patent: Mar. 10, 1987

[54] AIR LEAK DETECTION CHAMBER FOR DRAINAGE DEVICE

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 704,280

[22] Filed: Feb. 22, 1985

[51] Int. Cl.$^4$ ............................................. A61M 1/00
[52] U.S. Cl. ..................................... 604/321; 137/205
[58] Field of Search ............... 604/317, 323, 324–326, 604/122–127, 251–254; 137/205; 73/234; 141/48, 59; 55/193, 248, 251, 441

[56] References Cited

U.S. PATENT DOCUMENTS

| | | | |
|---|---|---|---|
| 3,559,647 | 2/1971 | Bidwell et al. | 141/59 |
| 3,683,913 | 8/1972 | Kurtz et al. | 604/321 |
| 4,188,948 | 2/1980 | Swinton | 604/126 |
| 4,258,824 | 3/1981 | Kurtz et al. | 604/321 |
| 4,296,748 | 10/1981 | Kurtz et al. | 604/319 |
| 4,455,141 | 6/1984 | Todd | 604/321 |
| 4,469,484 | 9/1984 | Kurtz et al. | 604/321 |

Primary Examiner—C. Fred Rosenbaum
Assistant Examiner—Mario Costantino
Attorney, Agent, or Firm—Larson and Taylor

[57] ABSTRACT

An air leak detection chamber is provided which is adapted to be attached to a conventional pleural drainage device. The air leak detection chamber has a pair of passageways which are connected in series in the passageway of the pleural drainage device leading from the underwater seal or from the oneway valves disposed in the passageway leading from the collection chamber to the suction source of the pleural drainage device. The detection chamber has a water filled tube therein and any air passing from the pleural drainage device will displace the water within the tube. Thus, a physician may readily observe the volume of air passing from the pleural cavity of a patient and determine the extent of any air leak in the pleural cavity.

5 Claims, 3 Drawing Figures

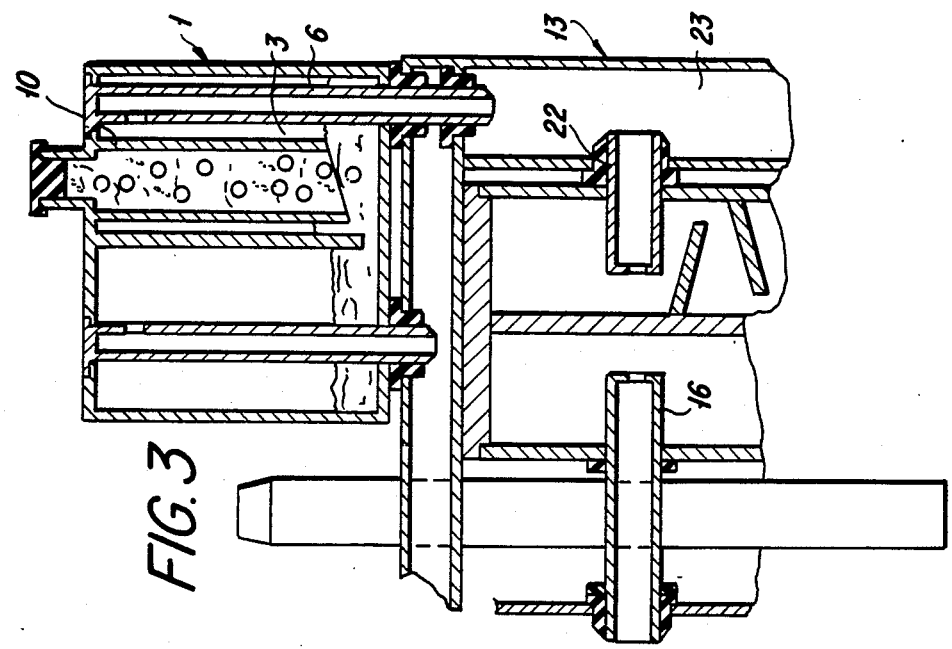
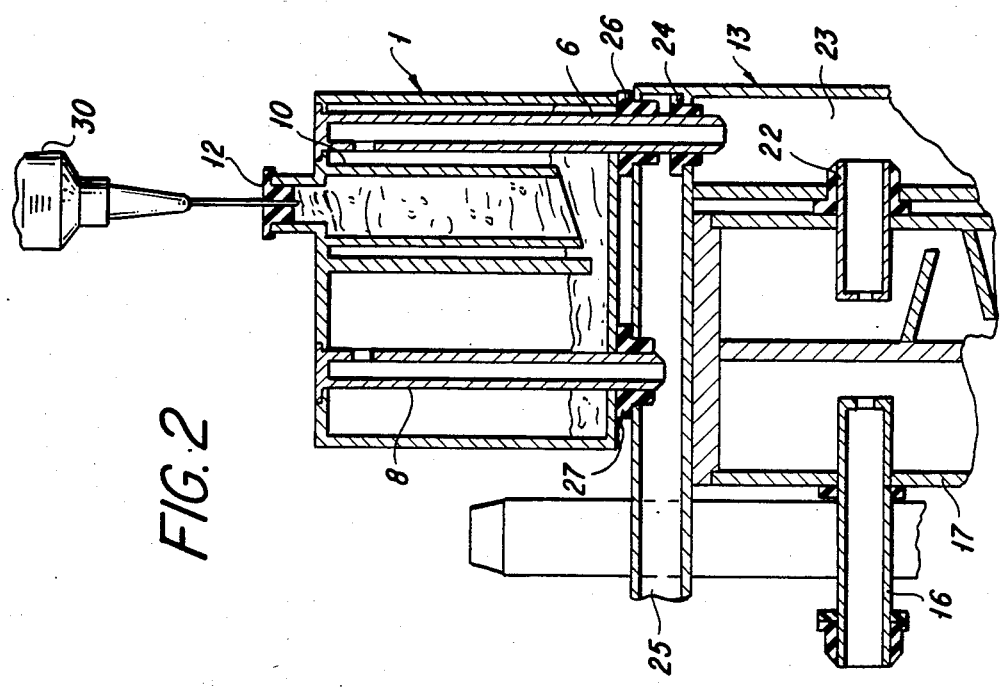

AIR LEAK DETECTION CHAMBER FOR DRAINAGE DEVICE

BACKGROUND OF THE INVENTION

The present invention relates to an air leak detection chamber for use with a drainage device and more particularly to a device for indicating the passage of air through an underwater seal in a pleural drainage device and for indicating the total volume of air passing through the seal.

There have been a number of prior art patents issued on pleural drainage devices utilizing underwater seals to insure that atmospheric air cannot enter the pleural cavity of the patient to which the device is connected. U.S. Pat. Nos. 3,363,626 and 3,363,627 are typical of prior art pleural drainage devices including a collection chamber, underwater seal chamber and manometer chamber. A thoracotomy tube provides a passageway to interconnect the collection chamber with the pleural cavity of a patient and an opening is provided on the other side of the underwater seal to connect the drainage device to a source of suction. In operation the water level within the manometer chamber regulates the suction from the suction source to provide the desired degree of vacuum to the collection chamber and pleural cavity of the patient. Fluids from the pleural cavity collect in the collection chamber and gases from the pleural cavity pass through the underwater seal in the form of bubbles.

Pleural drainage devices such as described above function well in maintaining the desired degree of vacuum in the pleural cavity and the underwater seal provides a means to prevent the entry of atmospheric air into the pleural cavity should, for example, the device become detached from the suction source. It has been found that the underwater seal also performs a further important function. Physcans examining the underwater seal can observe the passage of air bubbles through the seal and by monitoring the frequency of the passage of such bubbles can make a judgement as to the degree of air leak in the pleural cavity of the patient. This use of the underwater seal as a diagnostic tool is important and the present invention enhances this function so that the physician can more accurately determine the condition of the patient even though his time spent with the patient is relatively limited.

The difficulty encountered with prior art drainage devices occurs when, for example, no bubbles pass through the underwater seal or only a single bubble passes through the seal during the period of time the physcan is with the patient. Under these circumstances, the physician cannot estimate the total volume of air passing out from the pleural cavity of the patient over a given period of time.

SUMMARY OF THE INVENTION

The present invention provides a means for indicating the presence of an air leak in the pleural cavity and for measuring the total amount of air passing out of the pleural cavity. The air leak detector comprises a container having a partition therein dividing the container into two compartments with an interconnecting passageway between the compartments at the lower end of the partition. The device is provided with a tubular passageway within each compartment, each of the tubular passageways being open at the upper end and extending outwardly of the container for connection with a pleural drainage device. There is provided an air leak detection chamber within one of the compartments and initially water fills the lower end of the container. The device is connected in series in the passageway interconnecting the collection chamber of a pleural drainage device with a suction source. In a drainage device such as shown in U.S. Pat. No. 3,363,626 it would be connected in series in the large arm of the underwater seal. In pleural drainage devices utilizing oneway valves in place of underwater seals the device would be inserted in the passageway leading to the suction source immediately adjacent the oneway valves. The upper end of the air leak detection chamber is provided with a puncturable diaphragm and tne needle of a syringe is inserted into this chamber to withdraw all the air from the chamber and to fill the chamber with water from the water in the lower end of the container. The device is then ready for use. An air leak within the pleural cavity will cause air to pass through the collection chamber of the pleural drainage device and through the underwater seal or past the oneway valves which may be used in place of a seal. The air will then pass into the air leak detection device and will displace the water within the air leak detection chamber. Thus, the presence of air within the air leak detection chamber shows that there is a pleural air leak in the patient and the volume of air in the chamber shows the degree of air leak from the time at which the chamber was initially filled with water.

Other objects and many of the attendant advantages of the present invention will become more readily apparent upon consideration of the following detailed specification in connection with the accompanying drawings.

BRIEF DESCRIPTION OF THE DRAWINGS

FIG. 2 is a view similar to FIG. 1 but showing the detection chamber in its attached position; and FIG. 3 is a view showing the detection chamber in operation.

DESCRIPTION OF THE PREFERRED EMBODIMENT

Figure 1:
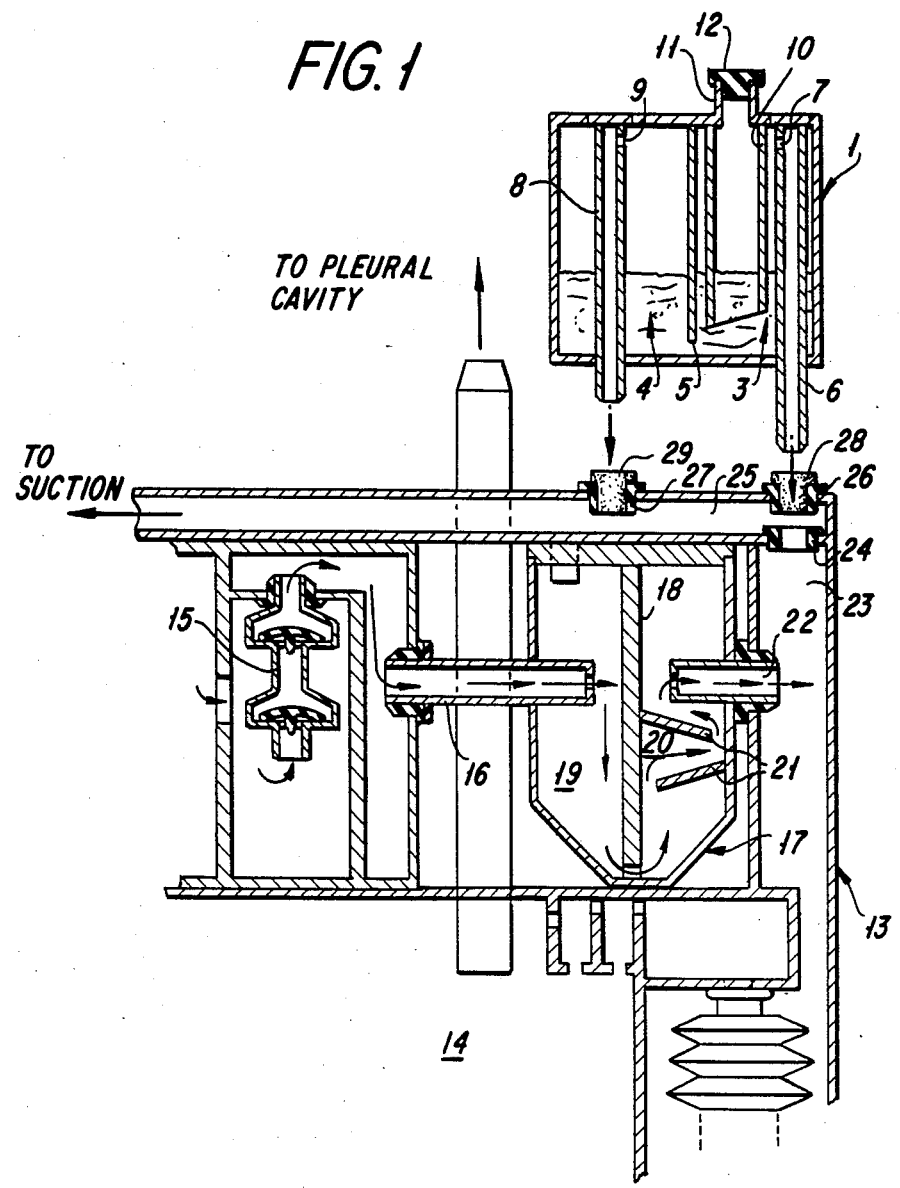
FIG. 1 is a side elevation in section showing the air leak detection chamber and one type of pleural drainage device to which the detection chamber may be attached.

Referring now more specifically to the drawings wherein like numerals indicate like parts throughout the several views, the air leak detection chamber is shown as comprising a container 1 in which is disposed a central partition 2 which is attached to the top wall and extends from one side wall to the other side wall within container 1 so as to form a chamber 3 and 4 on opposite sides of the partition. A passageway 5 is formed beneath the bottom wall of partition 2 to provide interconnection between the compartments 3 and 4.

Within compartment 3 there is provided a tubular passageway 6 which is attached to the upper end of the container 1 and projects through the bottom wall of the container. The lower end of the tube 6 is open and an opening 7 is provided adjacent the upper end of the passageway 6 so as to provide communication between compartment 3 and the passageway. A similar tubular element 8 is provided within compartment 4 and this element is attached to the top wall of container 1 and projects through an opening in the bottom wall. It will be noted that the tubular element 8 extends through the bottom wall a lesser distance than does the tubular element 6. An opening 9 is provided adjacent the upper end of element 8 so as to provide a communicating passageway between the interior of compartment 4 and the passageway formed in element 8.

An air leak detection chamber 10 is provided within the compartment 3. This air leak detection chamber comprises a tube 10 which is open ended and has the upper end thereof affixed to the top wall of container 1. The lower end of the tube 10 is open as shown and is provided with an angularly formed base. The upper end of the container 1 is formed with a tubular spigot-like projection and the upper end of the spigot 11 is closed by a puncturable diaphragm 12.

The air leak detection chamber shown is adapted to be connected to a pleural drainage device. In the embodiment shown the device is connected with a pleural drainage device such as disclosed in copending application Ser. No. 606,968, filed May 4, 1984, for Surgical Drainage Apparatus. Only a portion of the pleural drainage device disclosed in that application is shown herein. The pleural drainage device comprises a container 13 having a collection chamber 14 and a passageway leading from the collection chamber passes through a series of oneway valves 15 and through tube 16 into a bubble detection chamber 17. The bubble detection chamber comprises a container having a central partition 18 therein so as to form compartments 19 and 20 on either side of the partition. The lower end of partition 18 is spaced from the bottom of container 17 so as to form a passageway interconnecting compartments 19 and 20. Baffles are provided in chamber 20 as shown at 21 and an exit passageway 22 extends from the interior of compartment 20 to a passageway 23. Passageway 23 interconnects through grommet 24 with a passageway 25 extending through a suction regulator to the suction source.

The top wall of the pleural drainage device 13 is provided with a pair of openings having grommets 26 and 27 disposed therein. When the air leak detection chamber is not attached to the drainage device the openings within the grommets 26 and 27 are sealed by plugs 28 and 29.

The pleural drainage device 13 as shown in FIG. 1 operates in a manner as fully described in application Ser. No. 606,968 when the air leak detection chamber 1 is not attached to the device. The bubble detection chamber 17 which has a small amount of water in the lower end will show by bubbling air passing from the pleural cavity of a patient through the collection chamber and oneway valves 15 so that the presence of an air leak can be readily detected by the presence of such bubbles. However, as the air leak in the pleural cavity is healed the frequency of such bubbling within the bubble chamber 17 will be reduced and at that point the air leak detection chamber will be attached so that the presence of any air leak, however minute, can be determined.

While the air leak detection chamber is shown in the drawings herein as being attached to a pleural drainage device having oneway valves in place of the more conventional underwater seal, it is apparent that the device can be used equally as well with a drainage device having an underwater seal. In such a case, the air leak detection chamber is connected in the large arm of the underwater seal or in a passageway connecting the large arm of the underwater seal with the suction source. Thus, any air passing through the underwater seal will necessarily pass through the air leak detection chamber in the same manner as disclosed herein.

In FIG. 2 the air leak detection chamber 1 is shown in its attached position with the pleural drainage device 13. The plugs 28 and 29 are removed and the projecting ends of tubes 6 and 8 are pressure fit within the grommets 24, 26 and 27 as shown in FIG. 2. Thus, any air passing from the collection chamber through passageway 16, through bubble detector chamber 17 and passageway 22 into passageway 23 must necessarily pass through the air leak detection chamber 1 as this is the only path for air flow to the suction source.

When the air leak detection chamber is attached to the pleural drainage device 13 as shown in FIG. 2 the needle of a syringe 30 is passed through the puncturable plug 12 and all air is drawn from the tube 10 so that the tube 10 is completely filled with water. When the tube 10 is filled with water the device is ready for operation.

As shown in FIG. 3 any air passing from the pleural cavity of the patient will pass through passageways 16 and 22 and through tube 16 into compartment 3. At that point the air will bubble up through the lower end of tube 10 and displace water from the upper end of the tube. Thus, any air passing from the pleural cavity after the air leak detection device 1 is attached to the pleural drainage device will be accumulated within the tube 10. In this manner the physician can readily observe the condition of tube 10 and determine whether the patient's pleural cavity is still leaking even though he does not see any bubbles passing through the bubble detection chamber 17 at the particular time of his visit. The device may be readily reset by the physician at the time of each visit simply by refilling the tube 10 with water by the use of syringe 30. By virtue of the present invention the physician can be assured that any air leak from the pleural cavity has healed by the time of discharge of the patient and that there will be no unnecessary delay in releasing a patient occasioned by reason of uncertainty as to the condition of an air leak in the pleural cavity.

Obviously many modifications and variations of the present invention are possible in light of the above teachings.

What is claimed as new and is desired to be secured by Letters Patent is:

1. An air leak detector for a drainage device wherein the drainage device includes a collection chamber for collecting fluids and a passageway leading from the collection chamber, said air leak detector including a container having a first compartment and a second compartment, partition means separating said compartments and having an opening at the lower end thereof to provide a passageway between the first and second compartments, means in said container providing a path for gas flow from the collection chamber into said first compartment and from said second compartment into said passageway leading from the collection chamber, and air leak detection means within said container for collecting gas passing out of said collection chamber, said air leak detection means including a separate chamber disposed in said first compartment and having a closed upper end and an open lower end.

2. An air leak detector according to claim 1 wherein the open lower end of said separate chamber is disposed above the opening at the lower end of said partition means.

3. An air leak detector according to claim 1 wherein the closed upper end of said separate chamber comprises a puncturable diaphragm.

4. An air leak detector according to claim 1 wherein said means in said container providing a path for gas flow comprises tubes extending through a wall of said container and having openings in said tubes above the lower end of the container.

5. An air leak detector according to claim 4 and further including spaced openings in said passageway leading from the collection chamber, each of said spaced openings receiving one of said tubes whereby said air leak detector comprises a pathway for air flow bypassing the portion of said passageway between the spaced openings therein.

* * * * *